(12) United States Patent
Zagury et al.

(10) Patent No.: US 8,632,781 B2
(45) Date of Patent: Jan. 21, 2014

(54) IMMUNOGENIC COMPOUNDS COMPRISING PEPTIDES OF IL1β

(75) Inventors: Jean-Francois Zagury, Paris (FR); Marie-Christophe Boissier, Paris (FR); Natacha Bessis, Paris (FR)

(73) Assignee: Vaxconsulting, Paris (FR)

( * ) Notice: Subject to any disclaimer, the term of this patent is extended or adjusted under 35 U.S.C. 154(b) by 0 days.

(21) Appl. No.: 13/004,526

(22) Filed: Jan. 11, 2011

(65) Prior Publication Data

US 2011/0182922 A1    Jul. 28, 2011

Related U.S. Application Data

(62) Division of application No. 10/590,905, filed as application No. PCT/US2005/005890 on Feb. 25, 2005, now Pat. No. 7,892,558.

(60) Provisional application No. 60/547,848, filed on Feb. 27, 2004.

(51) Int. Cl.
  *A61K 39/00*    (2006.01)
(52) U.S. Cl.
  USPC .......... 424/185.1; 530/317; 530/326; 530/327
(58) Field of Classification Search
  None
  See application file for complete search history.

(56) References Cited

U.S. PATENT DOCUMENTS

| 5,217,714 A | 6/1993 | Imura et al. |
|---|---|---|
| 5,519,119 A | 5/1996 | Yamada et al. |
| 5,795,859 A | 8/1998 | Rathjen et al. |
| 6,207,642 B1 | 3/2001 | Wiley |
| 6,881,408 B1 * | 4/2005 | Heinrich et al. ........... 424/140.1 |

FOREIGN PATENT DOCUMENTS

| DE | 69027121 T3 | 8/2001 |
|---|---|---|
| EP | 0288088 A | 10/1988 |
| EP | 569042 A1 * | 11/1993 |
| WO | 9006946 A | 6/1990 |
| WO | 9846642 A1 | 10/1998 |
| WO | WO 9922763 A2 * | 5/1999 |
| WO | WO 9951744 A2 * | 10/1999 |
| WO | 03084979 A | 10/2003 |

OTHER PUBLICATIONS

Brinckerhoff et al. Terminal modifications inhibit proteolytic degradation of an immunogenic MART-1(27-35) peptide: implications for peptide vaccines. Int J Cancer. Oct. 29, 1999;83(3):326-34.*
Hertz et al. Active vaccination against IL-5 bypasses immunological tolerance and ameliorates experimental asthma. J Immunol. Oct. 1, 2001;167(7):3792-9.*
Boraschi et al. Structure-function relationship of interleukin-1 giving new insights for its therapeutic potential. Biotherapy. 1989;1(4):377-89.*
Smith et al., A single amino acid difference between human and monkey interleukin (IL)-1beta dictates effective binding to soluble type II IL-1 receptor, J. Biol Chem, 277(49)47619-47625 (2002).

* cited by examiner

*Primary Examiner* — Gregory S Emch
(74) *Attorney, Agent, or Firm* — Browdy and Neimark, PLLC

(57) ABSTRACT

The present invention relates to peptides derived from the proinflammatory cytokines, interleukin-1β (IL1β) and tumor necrosis factor α (TNFα), and their use in human or veterinary therapy, such as to generally treat diseases linked to the overproduction of IL1β or TNFα as well as acute or chronic inflammatory diseases, rheumatoid arthritis, septic shock, autoimmune diabetes, graft rejection in the host, etc.

18 Claims, 1 Drawing Sheet

SEQUENCE LISTING

<160> NUMBER OF SEQ ID NOS: 16

<210> SEQ ID NO 1
<211> LENGTH: 16
<212> TYPE: PRT
<213> ORGANISM: Artificial
<220> FEATURE:
<223> OTHER INFORMATION: synthetic

<400> SEQUENCE: 1

Val Ser Arg Phe Ala Ile Ser Tyr Gln Glu Lys Val Asn Leu Leu Ser
1               5                   10                  15

<210> SEQ ID NO 2
<211> LENGTH: 16
<212> TYPE: PRT
<213> ORGANISM: Artificial
<220> FEATURE:
<223> OTHER INFORMATION: synthetic

```
<400> SEQUENCE: 2

Ile Ser Arg Ile Ala Val Ser Tyr Gln Thr Lys Val Asn Leu Leu Ser
1               5                   10                  15

<210> SEQ ID NO 3
<211> LENGTH: 15
<212> TYPE: PRT
<213> ORGANISM: Artificial
<220> FEATURE:
<223> OTHER INFORMATION: synthetic

<400> SEQUENCE: 3

Tyr Ile Ser Thr Ser Gln Ala Glu His Lys Pro Val Phe Leu Gly
1               5                   10                  15

<210> SEQ ID NO 4
<211> LENGTH: 15
<212> TYPE: PRT
<213> ORGANISM: Artificial
<220> FEATURE:
<223> OTHER INFORMATION: synthetic

<400> SEQUENCE: 4

Tyr Ile Ser Thr Ser Gln Ala Glu Asn Met Pro Val Phe Leu Gly
1               5                   10                  15

<210> SEQ ID NO 5
<211> LENGTH: 12
<212> TYPE: PRT
<213> ORGANISM: Artificial
<220> FEATURE:
<223> OTHER INFORMATION: synthetic

<400> SEQUENCE: 5

Asp Tyr Leu Asp Phe Ala Glu Ser Gly Gln Val Tyr
1               5                   10

<210> SEQ ID NO 6
<211> LENGTH: 12
<212> TYPE: PRT
<213> ORGANISM: Artificial
<220> FEATURE:
<223> OTHER INFORMATION: synthetic

<400> SEQUENCE: 6

Lys Tyr Leu Asp Phe Ala Glu Ser Gly Gln Val Tyr
1               5                   10

<210> SEQ ID NO 7
<211> LENGTH: 16
<212> TYPE: PRT
<213> ORGANISM: Artificial
<220> FEATURE:
<223> OTHER INFORMATION: synthetic

<400> SEQUENCE: 7

Val Lys Ser Leu Asn Cys Thr Leu Arg Asp Ser Gln Gln Lys Ser Leu
1               5                   10                  15

<210> SEQ ID NO 8
<211> LENGTH: 13
<212> TYPE: PRT
<213> ORGANISM: Artificial
<220> FEATURE:
<223> OTHER INFORMATION: synthetic

<400> SEQUENCE: 8
```

```
Ser Phe Val Gln Gly Glu Glu Ser Asn Asp Lys Ile Pro
1               5                   10

<210> SEQ ID NO 9
<211> LENGTH: 18
<212> TYPE: PRT
<213> ORGANISM: Artificial
<220> FEATURE:
<223> OTHER INFORMATION: synthetic

<400> SEQUENCE: 9

Asn Tyr Pro Lys Lys Lys Met Glu Lys Arg Phe Val Phe Asn Lys Ile
1               5                   10                  15

Glu Ile

<210> SEQ ID NO 10
<211> LENGTH: 11
<212> TYPE: PRT
<213> ORGANISM: Artificial
<220> FEATURE:
<223> OTHER INFORMATION: synthetic

<400> SEQUENCE: 10

Ile Thr Asp Phe Thr Met Gln Phe Val Ser Ser
1               5                   10

<210> SEQ ID NO 11
<211> LENGTH: 16
<212> TYPE: PRT
<213> ORGANISM: Artificial
<220> FEATURE:
<223> OTHER INFORMATION: synthetic

<400> SEQUENCE: 11

Ile Arg Gln Leu His Tyr Arg Leu Arg Asp Glu Gln Gln Lys Ser Leu
1               5                   10                  15

<210> SEQ ID NO 12
<211> LENGTH: 13
<212> TYPE: PRT
<213> ORGANISM: Artificial
<220> FEATURE:
<223> OTHER INFORMATION: synthetic

<400> SEQUENCE: 12

Ser Phe Val Gln Gly Glu Pro Ser Asn Asp Lys Ile Pro
1               5                   10

<210> SEQ ID NO 13
<211> LENGTH: 18
<212> TYPE: PRT
<213> ORGANISM: Artificial
<220> FEATURE:
<223> OTHER INFORMATION: synthetic

<400> SEQUENCE: 13

Gln Tyr Pro Lys Lys Lys Met Glu Lys Arg Phe Val Phe Asn Lys Ile
1               5                   10                  15

Glu Val

<210> SEQ ID NO 14
<211> LENGTH: 11
<212> TYPE: PRT
<213> ORGANISM: Artificial
<220> FEATURE:
<223> OTHER INFORMATION: synthetic
```

-continued

```
<400> SEQUENCE: 14

Ile Ile Asp Phe Thr Met Glu Ser Val Ser Ser
1               5                   10

<210> SEQ ID NO 15
<211> LENGTH: 18
<212> TYPE: PRT
<213> ORGANISM: Artificial
<220> FEATURE:
<223> OTHER INFORMATION: synthetic

<400> SEQUENCE: 15

Cys Val Ser Arg Phe Ala Ile Ser Tyr Gln Glu Lys Val Asn Leu Leu
1               5                   10                  15

Ser Cys

<210> SEQ ID NO 16
<211> LENGTH: 18
<212> TYPE: PRT
<213> ORGANISM: Artificial
<220> FEATURE:
<223> OTHER INFORMATION: synthetic

<400> SEQUENCE: 16

Tyr Cys Tyr Ile Ser Thr Ser Gln Ala Glu His Lys Pro Val Phe Leu
1               5                   10                  15

Gly Cys
```

IMMUNOGENIC COMPOUNDS COMPRISING PEPTIDES OF IL1β

BACKGROUND OF THE INVENTION

1. Field of the Invention

The present invention relates to new peptides derived from the proinflammatory cytokines Interleukin-1 beta (IL1β) and Tumor Necrosis Factor alpha (TNFα) and their use in human or veterinary therapy. The diseases targeted by these therapeutic uses can be in particular rheumatoid polyarthritis, septic shock, auto-immune diabetes, graft rejection in the host, and also acute or chronic inflammatory diseases, and more generally, diseases linked to the overproduction of ILβ or TNFα cytokines.

2. Description of the Related Art

Active anti-cytokine immunization is an active immunotherapy strategy developed since 1990 by Zagury et al. which is based in particular on Patent Application WO 92/22577. This idea was taken up by several scientific teams which have published in international scientific journals, active immunizations against the entire IFNα protein multimerized by treatment with glutaraldehyde (Gringeri et al., JAIDS 1999; 20:358-70), a chimeric TNFα protein consisting of coupling the native TNFα protein with a T epitope of ovalbumin (Dalum at al., Nature Biotechnology, 1999; 17:666-69), against entire IL9 coupled with KLH (Richard et al., PNAS, 2000; 97:767-72) or also chimeric entire IL5 with a T epitope of tetanus toxin (Hertz et al., J. Immunol, 2001; 167:3792-99).

These approaches have confirmed the feasibility of autologous anti-cytokine immunizations, but these few successes obscure the unsuccessful tests described by certain authors: certain cytokines do not allow sufficiently protective and clinically effective antibodies to be obtained, and the same cytokine prepared in a form which is effective in one manner, will not be effective in another (Richard et al., PNAS, 2000; 97:767-72).

In trying to explain this phenomenon, the Applicant has observed that to date all the authors have used entire cytokines (optionally slightly modified), which leads to difficulties in particular at the following levels:
- dilution of the immunogenic power of the antigenic determinants of interest
- possible genesis of facilitating antibodies in vivo (E response).
- possible genesis of autoimmune reaction to the potential T epitopes present in the entire cytokine (autoimmune T reaction).

This is why the Applicant has previously claimed families of peptides of limited size between 5 and 40 amino acids originating from cytokines and which have an antigenic power making it possible to generate antibodies against the native cytokine (Patent Application PCT/FR03/01120). EP-A-0218531 also described IL1 peptides used for the preparation of antibodies.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The Applicant has evaluated certain peptides of the IL1β, and TNF cytokines with a size comprised between 10 and 30 residues and has demonstrated that these peptides were not only antigenic, but that they were also effective as immunogens for protecting in vivo against diseases linked to the overproduction of these cytokines. The present Application therefore claims peptides of a size comprised between 5 and 30 amino acids, originating from murine or human IL1β and TNFα cytokines or those of any other species of mammal, and their use in humans or animals (in this case veterinary use) for preventing or treating diseases linked to the overproduction of these cytokines. The present Application also claims the production of monoclonal or oligoclonal antibodies from these peptides and the use of these antibodies for therapeutic or preventive administration to humans or animals (veterinary application).

DETAILED DESCRIPTION OF THE INVENTION

Figure 1:
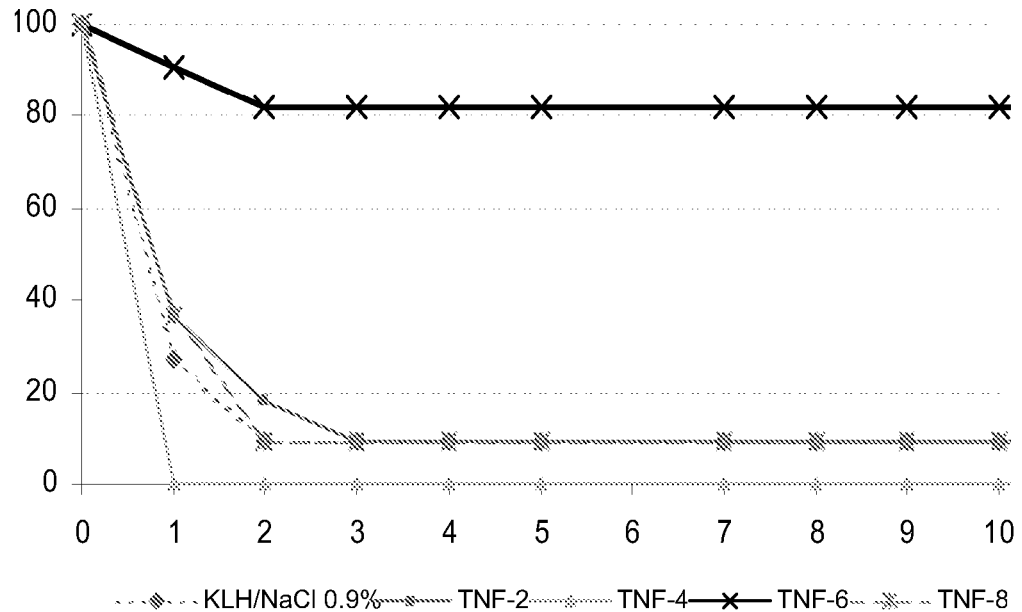
FIG. 1 is a graph showing survival of mice immunized against peptides and subjected to septic shock.

The cytokine peptides according to the invention originate from or are derived from the IL1β and TNFα cytokines. By "originate" is meant that their amino acid sequence is identical to that of the cytokine. By "are derived" is meant that their amino acid sequence is mostly identical to that of the cytokine but can comprise a few differences as will be seen hereafter.

The above cytokine peptides advantageously comprise more than 5, in particular more than 7, particularly more than 9 and quite particularly more than 11 amino acids.

Under other preferential conditions for implementing the invention, the above cytokine peptides comprise less than 30, advantageously less than 25, in particular less than 20, more particularly less than 18 amino acids.

The Applicant has demonstrated that the peptide area:

80 VSRFAISYQEKVNLLS 95 (SEQ ID NO:1) of the murine TNFα cytokine makes it possible to engender antibodies by active immunization, capable of blocking TNFα-dependent septic shock in mice (Experiment 1). The corresponding sequence of the human cytokine is 75% homologous:

80 ISRIAVSYQTKVNLLS 95        (SEQ ID NO: 2)

The Applicant has also demonstrated that the peptide area:

121 YISTSQAEHKPVFLG 135 (SEQ ID NO:3) of the murine IL1β cytokine makes it possible to engender antibodies by active immunization, capable of blocking collagen arthritis induced in mice (Experiment 2). The corresponding sequence in humans is 80% homologous:

121 YISTSQAENMPVFLG 135        (SEQ ID NO: 4)

Loetasoher et al. (J Biol Chem, 1993, 268:26350-357) have shown by site specific mutagenesis experiments that the 143-147 region of TNFα could be important in the interaction with the p55 receptor of TNFα, and the present invention also claims the immunization against B epitopes of this region by means of peptides having a significant homology, be they xenogenic or mutant in relation to the human or animal cytokine sequence. The sequence corresponding to this area in humans is:

```
140 DYLDFAESGQVY 150      (SEQ ID NO: 5)
``` and in mice:

```
140 KYLDFAESGQVY 150      (SEQ ID NO: 6)
```

Evans et al. Biol Chem, 1995, 270:11477-83) have also explained by site specific mutagenesis experiments that other regions of IL1β could be important in the interaction with the receptor, and the present invention also claims immunization against B epitopes of these regions by means of peptides having a significant homology, be they xenogenic or mutants in relation to the targeted human or animal cytokine sequence. The sequences corresponding to this area in humans are:

```
  3 VKSLNCTLRDSQQKSL 18   (SEQ ID NO: 7)
 45 SFVQGEESNDKIP 57      (SEQ ID NO: 8)
 89 NYPKKKMEKRFVFNKIEI 106 (SEQ ID NO: 9)
143 ITDFTMQFVSS 153       (SEQ ID NO: 10)
``` and in mice:

```
  3 IRQLHYRLRDEQQKSL 18   (SEQ ID NO: 11)
 45 SFVQGEPSNDKIP 57      (SEQ ID NO: 12)
 89 QYPKKKMEKRFVFNKIEV 106 (SEQ ID NO: 13)
142 IIDFTMESVSS 152       (SEQ ID NO: 14)
```

It has been possible to create autologous antibodies against the latter peptides of mice by active immunization.

Experiments 1 and 2 hereafter, carried out by the Applicant, demonstrate the therapeutic ability in vivo of the antipeptide active immunization approach with peptides of a size less than 30 residues. The Applicant claims these peptides and their derivatives for also carrying out active immunizations allowing the generation of antibodies targeting these epitopes of the TNFα and IL1b cytokines in order to block the interaction of the cytokine with its receptor.

As is known by a person skilled in the art of immunology, modifications of the natural peptide chains are possible without however modifying the nature of the immunological properties of the immunogenic peptides. Derivatives of cytokine peptides can therefore also be mentioned, which are highly homologous to these natural sequences, for example having more than 50% homology, in particular more than 70% homology, and preferably more than 80% homology or even more than 90% homology with the corresponding native peptide whilst retaining the immunological properties of this epitopic site of the native peptide. In particular homologous sequences of cytokines of other mammals can be used in order to obtain a xenogenic and not only an autologous protective reaction in an animal or human.

The cytokine peptide derivatives can contain modified residues, on condition that the modifications do not appreciably reduce the immunogenicity, either by adding chemical radicals (methyl, acetyl etc.) or by stereochemical modification (use of D series amino acids). The cytokine peptide derivatives should, like the cytokine peptides induce antibodies interacting with cytokine.

The cytokine peptide derivatives according to the invention can comprise one or more modifications in the amino acids of which they are constituted, such as deletions, substitutions, additions, or functionalizations (such as acylation) of one or more amino acids, to the extent that these modifications remain within the framework specified above (immunological characters). For example, in general the replacement of a leucine residue by an isoleucine residue does not modify such properties; the modifications should generally concern less than 40% of the amino acids, in particular less than 30%, preferably less than 20% and quite particularly less then 10% of the amino acids of the natural peptide. It is important that the antibodies induced by the modified peptides are active vis-à-vis native cytokine.

These modifications are within the scope of a person skilled in the art, who can verify the incidence of the modifications by simple tests. The immunogenicity of such modified derivatives can be evaluated by ELISA after immunization of mice, the antigen tested by ELISA being the entire cytokine or the immunizing cytokine peptide, or by cytokine-receptor bond blocking tests. The possible modifications preferably affect less than 8 amino acids, advantageously less than 6 amino acids, in particular less than 4 amino acids, and particularly 3 amino acids or less, such as 2 or 1 single amino acid.

A subject of the invention is also a compound characterized in that it contains at least one abovementioned cytokine peptide or cytokine peptide derivative. Such a compound can comprise identical peptide/derivative repetitions, or different peptide/derivative combinations, either in linear form or in the form of a candelabra structure or couplings mixed with carrier proteins. Such a compound can also be presented in cyclized form. Thus cytokine peptides or cytokine peptide derivatives according to the invention can for example be inserted into longer sequences of amino acids providing in particular a better conformation or combined with exogenous T epitopes (whether for protein or DNA immunizations).

They can advantageously be associated in a covalent manner with carrier proteins such as for example KLH.

The cytokine peptides according to the invention, due to their limited size, correspond in general to a small number of epitopes of the cytokine. When they are in particular inserted, combined or associated, the above compounds do not comprise other epitopes of said cytokine.

These cytokine peptides or cytokine derivatives can be included in any protein sequence which does not comprise homology with the other natural cytokine epitopes. For example, a cysteine can be added to the ends in order to confer a cyclic structure on the peptide. Another example is a peptide surrounded by sequences of T epitopes of the tetanus toxin. Yet another example can comprise a peptide corresponding to the sequence of the receptor binding site but where certain amino acids are replaced by their D series isomers in order to avoid their agonist effect. In fact, it can be optionally advantageous to use peptide derivatives which have no agonist activity on the receptor so that the immunogen does not interfere with the immune response.

In order to increase the immune response, these cytokine peptides or cytokine derivatives can be coupled to carrier proteins. The coupling methods and the carrier protein considered can be different according to the target peptide: they can for example be Keyhole Limpet Hemocyanin (KLH) protein and Tetanus Toxoid (TT) conjugated to the peptides by chemical methods well known to a person skilled in the art such as those of carbodiimide, glutaraldehyde or bis-diazotized benzidine coupling. The realization of these couplings can be facilitated by the addition or incorporation of amino acids into the sequence, such as for example lysines, histidines, tyrosines or cysteines. Such peptide compounds coupled to an exogenous T epitope (originating from plasmodium falciparum, KLH, etc.) whether chemically or genetically also come within the scope of the invention.

Network couplings of candelabra type or to molecules such as transferrin or ferritin can also be implemented in order to effectively stimulate the immune response.

The peptides according to the invention can in particular be produced by chemical synthesis or genetic engineering or any other suitable method. The synthesis of cyclic peptides, grafting, as needed, one or more amino acids at the end of the chain as cysteines in order to create a disulphide bridge makes it possible to recover part of the secondary structure that these peptide fragments possess in the three-dimensional structure of the protein.

The peptides according to the invention possess very useful pharmacological properties. In particular they possess remarkable anti-cytokine properties. These properties are illustrated hereafter in the experimental part. They justify the use of the peptides described above as a medicament.

This is why a subject of the invention is also medicaments characterized in that they are constituted by peptides or derivatives of the IL1β or TNFα cytokines or compounds as defined above, i.e. cytokine peptides or cytokine derivatives or immunogenic compounds as defined above for their use in a method of therapeutic treatment of the human or animal body, as well as the use of such a cytokine peptide or cytokine derivative or immunogenic compound for the preparation of a curative or preventive medicament intended for the treatment or prevention of diseases linked to an excess or to the presence of cytokines.

The medicaments according to the present invention are used for example in both the curative and preventive treatment of diseases linked to cytokine deregulation, whether rheumatoid polyarthritis, septic shock or any other disease where the blocking of IL1β or TNFα is curative. These are only a few examples, and a subject of the invention is also any treatment of the human or animal body based on active immunization (DNA or peptide) involving the peptide sequences mentioned above to the exclusion of other epitopes of the cytokines. These sequences can be modified as indicated in the present description, and the immunizations by DNA are carried out by simple translation from the genetic code.

The humoral immunity response can be evaluated by ELISA tests.

The immunogenic active ingredients according to the invention can be used as follows:

A cytokine peptide or cytokine derivative or immunogenic compound according to the present invention, is administered to a patient or to an animal, for example by sub-cutaneous or intramuscular route, in a sufficient quantity to be effective at a therapeutic level, to a subject needing such treatment. The dose administered can for example range from 1 to 1000 µg, in particular 10 to 500 µg, by sub-cutaneous route, once a month for three months, then periodically as a function of the induced serum antibodies count, for example every 2-6 months. In the same preparation two immunogenic molecules of the two cytokines can be administered if a still stronger blocking effect is to be obtained.

A subject of the invention is also the pharmaceutical compositions in particular the vaccines which contain at least one abovementioned cytokine peptide or cytokine derivative or immunogenic compound, as active ingredient.

As medicaments, a cytokine peptide or cytokine derivative or immunogenic compound of the invention can be incorporated into pharmaceutical compositions intended for any standard route in use in the field of vaccines, in particular by sub-cutaneous route, by intramuscular route, by intravenous route or by oral route. The administration can take place in a single dose or repeated once or more after a certain period of time.

This is why a subject of the present Application is also a curative or preventive pharmaceutical composition, characterized in that it comprises as active ingredient, one or more cytokine peptides or cytokine derivatives or immunogenic compounds, as defined above.

The immunogenic agent can be conditioned alone or mixed with an excipient or mixture of pharmaceutically acceptable excipients as an adjuvant. A subject of the present Application is more particularly a vaccine containing as immunogen, an abovementioned cytokine peptide or cytokine derivative or immunogenic compound.

A subject of the present invention is also a process for preparing a composition described above, characterized in that, according to methods known per se, the active ingredient or ingredients are mixed with acceptable, in particular pharmaceutically acceptable excipients.

The administration to a patient of a cytokine peptide or cytokine derivative or immunogenic compound according to the invention corresponds to an active immunotherapy.

It can also be useful to carry out passive immunotherapy, i.e. to provide a patient or a sick animal directly with the antibodies which they need. For this purpose, the peptides, derivatives and compounds defined previously can be used in order to produce monoclonal antibodies according to the usual techniques, human, murine or humanized, for example by conversion of B lymphocytes from a subject immunized by the Epstein-Barr virus or by the screening of antibody libraries. These antibodies by targeting the epitopes of the above peptides block the interaction of the cytokine with its receptor and thus make it possible to reduce the pathogenic effect of the cytokine in the disease. Oligoclonal antibodies can also be prepared by active immunization in animals such as horses for example, purified, and administered therapeutically to humans or animals.

The vaccine preparations can be packaged for the intranasal route in the form of gel with carbopol as excipient, nasal drops or spray and for the oral route in the form of gastroresistant capsules, sugar-coated tablets or gastroresistant granules.

In the case of DNA vaccine administered by systemic or mucosal route, the galenic presentation of the plasmid can be a suspension in a physiological liquid such as physiological PBS (phosphate buffered saline=PBS). The plasmids can be enclosed in biodegradable polymer (PLG, PLA, PCL) microspheres and administered in gastroresistant capsules for ingestion (oral route). The DNA can also be expressed in a bacterial, salmonella-type or viral-type, adenovirus or poxvirus living vector.

Finally, a subject of the present Application is a process for active immunization of patients characterized in that as immunogen, a cytokine peptide or cytokine derivative or immunogenic compound is used, as defined above, advantageously associated with a mineral, oily or synthetic immunity adjuvant.

The immunizations can be done in a standard fashion in particular by peptides or immunogenic compounds as conjugates preferably in the presence of an adjuvant, for example ISA 51 or Alum. The immunizations can be DNA-based (sequences homologous to the binding sites combined with exogenous T epitopes) using naked DNA or an expression vector containing an adapted promoter such as for example pCR3.1. The DNAs administered can be protected from the nucleases by the use of appropriate radicals (CpG etc.). In particular an initial DNA immunization can be followed by standard boosters using the peptide compounds.

The methods of treatment of the human or animal body described in this patent can include a cytokine peptide or cytokine derivative or immunogenic compound as defined above, and can include the monoclonal or oligoclonal antibodies as defined above.

The preferential conditions for using the peptides described above also apply to the other subjects of the invention referred to above.

Figure 2:
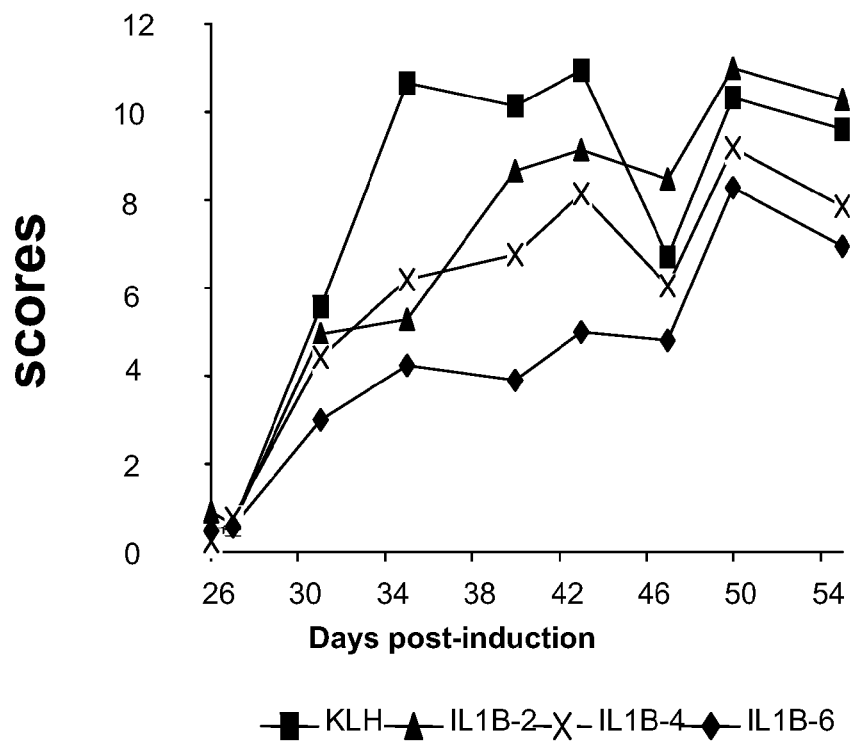
FIG. 2 is a graph showing average clinical scores of groups of mice immunized against peptides in a model of collagen arthritis.

FIG. 1 and FIG. 2 show the results of protection in vivo of the immunizations described in Experiments 1 and 2 for a TNFα peptide in TNFα-dependent septic shock and an IL1β peptide in collagen arthritis.

The experiments which follow illustrate the present invention.

Experiment 1

4 murine TNFα peptides coupled to the KLH carrier protein, including the cyclized peptide CVSRFAISYQEKVNLLSC (SEQ ID NO:15) called TNFα-6, were tested in a model of endotoxinic shock. For this purpose, Balb/c mice were preimmunized against these peptides on days D0, D0, D16, and D40. On day D50, the mice were subjected to shock, i.e. they were injected with LPS with Galactosamine. A control was carried out on mice immunized against KLH alone.

It is noted that all the mice died after two days, except for the group immunized against the TNFα-6 peptide where the mice were protected. The protection conferred by the immunization was very significant (p=0.008).

Experiment 2

3 murine IL1β peptides coupled to the KLH protein, including the cyclized IL1-6 peptide of sequence YCYISTSQAEHKPVFLGC (SEQ ID NO:16), were tested in a model of collagen arthritis. For this purpose, DBA1 mice were preimmunized against these peptides on days D0, D20, D40, DG0. On day D80 the mice were immunized against collagen in Freund's adjuvant, and similarly on day D95. The development of arthritis was monitored between day D100 and day D160: twice weekly, the mice were examined and a score was attributed to them as a function of the state of inflammation of their joints (0=no inflammation, 1=slight inflammation, 2=average inflammation, 3=strong inflammation).

It is noted that the control mice immunized by KLH alone exhibit strong inflammation (curve with squares) whereas the group of mice immunized against the IL1β-6 peptides (curve with diamonds) exhibit a strong protection level with respect to the control (p=0.0003, ANOVA test).

Experiment 3

6 groups of 4 mice were immunized against 20 ug of the murine IL1β peptides IRQLHYRLRDEQQKSL (group 1) (SEQ ID NO:11), SFVQGEPSNDKIP (group 2) (SEQ ID NO:12), QYPKKKMEKRFVFNKIEV (group 3) (SEQ ID NO:13), IIDFTMESVSS (group 4) (SEQ ID NO:14), and 20 ug of the murine TNFα peptide KYLDFAESGQVY (group 5) (SEQ ID NO:6) all coupled to KLH. Group 6 corresponds to mice immunized by KLH alone. A booster was administered on days D20 and D40. On day D50 the mice were sacrificed and the antibodies directed against the native mTNFα cytokine and the native mIL1β cytokine in the serums were measured by an ELISA test.

The averages obtained for each group are indicated in the table hereafter.

TABLE 1

|  | Anti-TNFα response Average | Anti-IL1β response Average |
|---|---|---|
| Group 1 | 0.13 | 1.5 |
| Group 2 | 0.15 | 1.9 |
| Group 3 | 0.18 | 1.6 |
| Group 4 | 0.12 | 0.8 |
| Group 5 | 1.3 | 0.31 |
| Group 6 | 0.10 | 0.15 |

It is therefore clear that these peptides are well capable of inducing antibodies recognizing the native cytokine. These antibodies are very specific since they recognize only the cytokine the sequence of which was used for the immunization.

What is claimed is:

1. An isolated immunogenic compound consisting of (a) a the peptide of less than 20 residues in length that comprises an amino acid sequence with more than 90% sequence identity to SEQ ID NO:7, coupled to (b) a heterologous carrier protein that increases the immunogenicity of the peptide in (a).

2. The immunogenic compound of claim 1, wherein the peptide is the human IL1β cytokine peptide consisting of the sequence of SEQ ID NO:7.

3. The immunogenic compound of claim 1, wherein the peptide of (a) is coupled to the heterologous carrier protein of (b) by chemical conjugation.

4. The immunogenic compound of claim 1, wherein the heterologous carrier protein is Keyhole Limpet Hemocyanin.

5. The immunogenic compound of claim 1, wherein the heterologous carrier protein is Tetanus Toxoid.

6. The immunogenic compound of claim 1, wherein one or more amino acids of said peptide are modified by cyclization, stereochemical modification or functionalization of one or more amino acids of said peptide.

7. The immunogenic compound of claim 6, wherein the functionalization is acylation.

8. An immunizing composition, comprising the immunogenic compound of claim 1 and an adjuvant.

9. An immunogenic compound consisting of (a) a peptide of less than 30 residues in length that comprises an amino acid sequence with more than 90% sequence identity to the amino acid sequence of SEQ ID NO:8, coupled to (b) a heterologous carrier protein that increases the immunogenicity of the peptide in (a).

10. The immunogenic compound of claim 9, wherein the peptide is the human IL1β cytokine peptide consisting of the sequence of SEQ ID NO:8.

11. The immunogenic compound of claim 9, wherein the peptide is less than 25 residues in length.

12. The immunogenic compound of claim 9, wherein the peptide is less than 20 residues in length.

13. The immunogenic compound of claim 9, wherein the peptide of (a) is coupled to the heterologous carrier protein of (b) by chemical conjugation.

14. The immunogenic compound of claim 9, wherein the heterologous carrier protein is Keyhole Limpet Hemocyanin.

15. The immunogenic compound of claim 9, wherein the heterologous carrier protein is Tetanus Toxoid.

16. The immunogenic compound of claim 9, wherein one or more amino acids of said peptide are modified by cyclization, stereochemical modification or functionalization of one or more amino acids of said peptide.

17. The immunogenic compound of claim 16, wherein the functionalization is acylation.

18. An immunizing composition, comprising the immunogenic compound of claim 9 and an adjuvant.

* * * * *